United States Patent
Kobayashi et al.

(10) Patent No.: US 7,943,209 B2
(45) Date of Patent: May 17, 2011

(54) LIQUID CRYSTAL MOLECULE, LIQUID CRYSTAL DISPLAY DEVICE, AND LIQUID CRYSTAL SPATIAL LIGHT MODULATION DEVICE

(75) Inventors: Ken Kobayashi, Kanagawa (JP); Hidehiko Takanashi, Kanagawa (JP); Rika Kotake, Kanagawa (JP)

(73) Assignee: Sony Corporation, Tokyo (JP)

( * ) Notice: Subject to any disclaimer, the term of this patent is extended or adjusted under 35 U.S.C. 154(b) by 2 days.

(21) Appl. No.: 12/568,826

(22) Filed: Sep. 29, 2009

(65) Prior Publication Data

US 2010/0079719 A1    Apr. 1, 2010

(30) Foreign Application Priority Data

Sep. 30, 2008   (JP) .................. 2008-253283

(51) Int. Cl.
| | |
|---|---|
| *C09K 19/20* | (2006.01) |
| *C09K 19/12* | (2006.01) |
| *C09K 19/30* | (2006.01) |
| *C09K 19/32* | (2006.01) |
| *C09K 19/34* | (2006.01) |
| *G02F 1/133* | (2006.01) |
| *C07F 7/04* | (2006.01) |
| *C07F 7/08* | (2006.01) |
| *C07F 7/18* | (2006.01) |

(52) U.S. Cl. ............ 428/1.1; 252/299.61; 252/299.62; 252/299.63; 252/299.64; 252/299.65; 252/299.66; 252/299.67; 349/184; 556/425; 556/437; 556/450; 556/451

(58) Field of Classification Search .............. 428/1.1; 252/299.61, 299.62, 299.63, 299.64, 299.65, 252/299.67; 349/184; 556/425, 437, 450, 556/451

See application file for complete search history.

(56) References Cited

U.S. PATENT DOCUMENTS 5,891,358 A    4/1999   Slaney et al.
(Continued)

FOREIGN PATENT DOCUMENTS

JP    64-083049    3/1989
(Continued)

OTHER PUBLICATIONS

Stephen Garoff and Robert B. Meyer; Electroclinic Effect at the A-C Phase Change in a Chira Smectic Liquid Crystal; Physical Review Letters; vol. 38, No. 15; Apr. 11, 1977.
(Continued)

*Primary Examiner* — Shean C Wu
(74) *Attorney, Agent, or Firm* — SNR Denton US LLP (57) ABSTRACT

A liquid crystal molecule includes a structure represented by Formula (1):

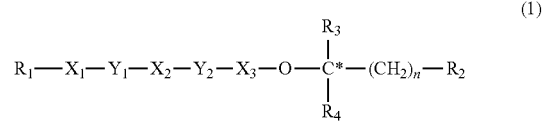

wherein $X_1$ in Formula (1) is represented by Formula (2);

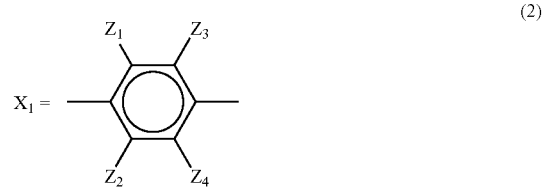

$X_2$ in Formula (1) is a group selected from Formula (3);

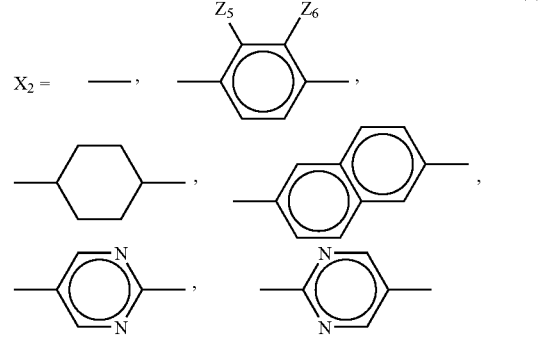

$X_3$ in Formula (1) is represented by Formula (4).

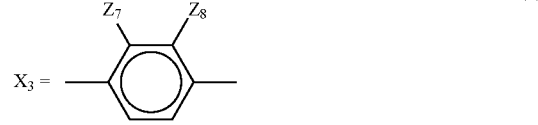

4 Claims, 3 Drawing Sheets

U.S. PATENT DOCUMENTS

| | | | |
|---|---|---|---|
| 6,300,454 B1 * | 10/2001 | Hanelt et al. | 528/27 |
| 7,615,165 B2 * | 11/2009 | Takanashi | 252/299.01 |
| 2008/0143950 A1 | 6/2008 | Takanashi | |

FOREIGN PATENT DOCUMENTS

| | | |
|---|---|---|
| JP | 2008-150334 | 7/2008 |
| JP | 09-507486 | 1/2011 |

OTHER PUBLICATIONS

J. Naciri et al.; Novel Ferroelectric and Electroclinic Organosiloxane Liquid Crystals; Chem. Mater.; 1995; 7, 1397-1402.

Japanese Patent Office Action dated Sep. 28, 2010 corresponding to Japanese Serial No. 2008-253283.

Bezborodov, V. S. et al., "Chiral Liquid Crystalline 3,6-disubstituted cyclohex-2-enones, their Derivatives and FLC Compositions Based upon Them", Liquid Crytals., Vo. 32, No. Jul. 2005, pp. 889-900.

\* cited by examiner

LIQUID CRYSTAL MOLECULE, LIQUID CRYSTAL DISPLAY DEVICE, AND LIQUID CRYSTAL SPATIAL LIGHT MODULATION DEVICE

BACKGROUND OF THE INVENTION

1. Field of the Invention

The present invention relates to a liquid crystal molecule, and to a liquid crystal display device and a liquid crystal spatial light modulation device that use the liquid crystal molecule.

2. Description of the Related Art

In recent years, active-matrix liquid crystal display devices (LCDs) such as thin film transistor (TFT) devices have come to be widely used in devices from small mobile units to large television sets. LCDs have been enhanced in terms of response speed by adopting techniques such as the impulse driving method. However, the LCDs are still inferior to plasma display panels (PDPs), field emission displays (FEDs), and the like in display quality regarding moving images due to, for example, moving-image blur arising from the slow response speed of the liquid crystal material itself.

Attempts have been made to enhance the speed from the current 60 Hz frame rate drive to 120 Hz or 240 Hz (high frame rate drive) and to enhance the moving-image display quality. The moving-image display quality of LCDs mostly depends on the response characteristics of the liquid crystal material itself, though partly depending on the drive system including TFTs. In other words, the above-mentioned problem is not fundamentally solved and the high frame rate drive is not realized unless the liquid crystal material has high-speed response.

Thus, there is a keen demand for a liquid crystal material that can support a high frame rate drive and exhibit high-speed response allowing the realization of a high moving-image display quality.

Examples of the liquid crystal that can achieve high-speed response include a nematic liquid crystal with a flexoelectric effect, a ferroelectric liquid crystal, and an antiferroelectric liquid crystal. The inventor of the present invention has paid attention to an electroclinic effect in a smectic A phase.

The electroclinic effect is a phenomenon in which the optical axis of liquid crystal molecules (longitudinal axis of liquid crystal molecules) uniaxially aligned in a smectic A phase is inclined in accordance with the intensity of an electric field applied (refer to Garoff et al., Physical Review Letters, Vol. 38, 1977, p. 848). When this type of cell is disposed between polarizing plates orthogonal to each other, transmitted light amount that is dependent on the angle (tilt angle) between the optical axes of the polarizing plate and the liquid crystal is obtained (refer to Formula (A)), and the maximum transmittance is obtained at a tilt angle of ±45°.

$$T/T_0 = \sin^2(2\theta) \times \sin^2(\pi \Delta n d/\lambda) \quad (A)$$

where $T$ is transmitted light amount, $T_0$ is incident light amount, $\theta$ is the angle (tilt angle) between the optical axes of the polarizing plate and the liquid crystal, $\Delta n$ is the birefringence of the liquid crystal, $d$ is the thickness of the liquid crystal layer, and $\lambda$ is the wavelength of the transmitted light.

Figure 5:
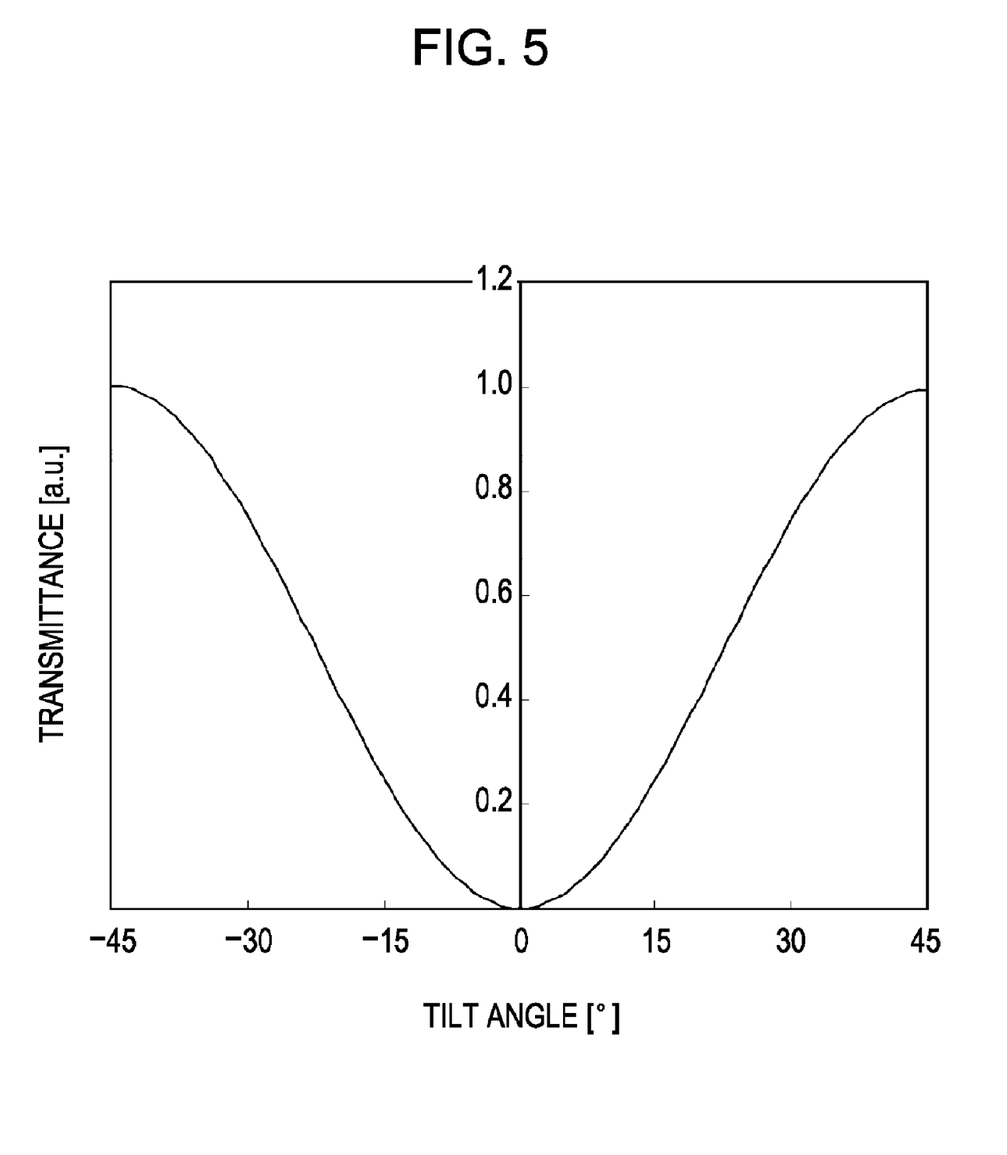
FIG. 5 is a graph showing a relationship between tilt angle and transmittance for a liquid crystal cell including liquid crystal molecules in a smectic A phase in which they are uniaxially aligned.

The dependence of transmittance on tilt angle in the case of a retardation ($=\Delta nd$) giving the maximum transmittance is calculated using Formula (A). FIG. 5 shows the result.

The response time in the electroclinic effect is as short as several microseconds to several tens of microseconds. Furthermore, it is advantageous that the inclination angle (tilt angle) of an optical axis is proportional to electric field intensity (i.e., voltage modulation of transmitted light is possible) when the electric field intensity is low. In other words, this is a display mode particularly suited to an active matrix drive.

However, the tilt angle in the electroclinic effect produced from existing liquid crystal materials is not so large, and sufficient optical modulation is not obtained.

Examples of a liquid crystal material that shows a large tilt angle include materials in which a siloxane is added to an achiral terminal end. This may be because the addition of a siloxane, which is a functional group that is larger in volume than ordinary alkyl chains and is flexible, to a terminal group of a molecule renders a core portion of the molecule more easily movable under the application of an electric field, the core portion contributing to optical modulation. According to Naciri et al., Chem. Mater. 1995, 7, pp. 1397-1402, liquid crystal molecules having a structure in which a siloxane is added to an achiral terminal end have a maximum tilt angle of 26°. However, the transmittance calculated from Formula (A) is about 60% at most, and the polarization is high because such a liquid crystal molecule has a nitro group as a polarization group. The transmittance is still insufficient in consideration of the practical use of display devices or the like.

Japanese Unexamined Patent Application Publication No. 2008-150334 discloses a liquid crystal molecule having an asymmetric carbon atom, and having a core portion with a terminal phenyl group and an organosiloxane that are opposite each other so as to sandwich the asymmetric carbon atom. However, since the terminal end of the liquid crystal molecule is an alkoxy-substituted phenyl group that does not have a functional group, such a liquid crystal molecule is not satisfactory in terms of a small tilt angle. Therefore, it is desired to further increase a tilt angle.

SUMMARY OF THE INVENTION

Accordingly, it is desirable to provide a liquid crystal molecule showing a large tilt angle in an electroclinic effect and achieving sufficient optical modulation.

It is also desirable to provide a liquid crystal display device and a liquid crystal spatial light modulation device that use a liquid crystal molecule showing a large tilt angle in an electroclinic effect and achieving sufficient optical modulation.

The inventor of the present invention found that a further increase in tilt angle can be achieved using a chemical compound obtained by adding an organosilane or organosiloxane structure to one chiral terminal end having an asymmetric carbon atom and by arranging a terminal phenyl group with a functional group on another chiral terminal end. Based on this finding, the inventor of the present invention has made intensive investigations to complete the present invention.

According to an embodiment of the present invention, there is provided a liquid crystal molecule having a structure represented by Formula (1):

(1)

wherein $X_1$ in Formula (1) is represented by Formula (2);

(2)

$X_2$ in Formula (1) is a group selected from Formula (3);

(3)

$X_3$ in Formula (1) is represented by Formula (4); and (4)

in Formulas (1) to (4), $R_1$ is a hydrocarbon group or an alkoxy group having a straight chain or a branched chain with 4 to 16 carbon atoms; $R_2$ is an organosiloxane or an organosilane with 1 to 6 silicon atoms that may have a branched chain; $R_3$ and $R_4$ different from each other are each H, F, Cl, Br, CN, $CH_3$, $CF_3$, or $OCH_3$; $Y_1$ and $Y_2$ are each -, —COO—, —$CH_2$—, —$CH_2O$—, —$C_2H_2$—, —$C_2$—, or —$CF_2O$—; $Z_1$ to $Z_4$ are each H, F, Cl, Br, OH, $NO_2$, CN, $CF_3$, $CH_3$, $C_2H_5$, $OCH_3$, or $OC_2H_5$; at least one of $Z_1$ to $Z_4$ is $CH_3$, $C_2H_5$, $OCH_3$, or $OC_2H_5$; $Z_5$ and $Z_6$ are each H, F, Cl, Br, OH, $NO_2$, CN, or $CF_3$; $Z_7$ and $Z_8$ are each H, F, Cl, Br, OH, $NO_2$, CN, or $CF_3$, excluding the case in which both $Z_7$ and $Z_8$ are H; n is an integer from 1 to 6; * represents a chiral center; and - represents a linking group.

According to another embodiment of the present invention, there is provided a liquid crystal molecule having a structure represented by Formula (5):

(5)

wherein, in Formula (5), $R_{11}$ is an alkoxy group having a straight chain or a branched chain with 4 to 16 carbon atoms; $R_{13}$ is F, Cl, Br, CN, $CH_3$, $CF_3$, or $OCH_3$; $Z_1$ to $Z_4$ are each H, F, Cl, Br, OH, $NO_2$, CN, $CF_3$, $CH_3$, $C_2H_5$, $OCH_3$, or $OC_2H_5$; at least one of $Z_1$ to $Z_4$ is $CH_3$, $C_2H_5$, $OCH_3$, or $OC_2H_5$; $Z_7$ and $Z_8$ are each H, F, Cl, Br, OH, $NO_2$, CN, or $CF_3$, excluding the case in which both $Z_7$ and $Z_8$ are H; n is an integer from 1 to 6; m is an integer from 1 to 5; and * represents a chiral center.

According to still another embodiment of the present invention, there is provided a liquid crystal display device including a pair of transparent substrates; a liquid crystal layer filled with the liquid crystal molecules according to an embodiment of the present invention and formed between the pair of substrates, the liquid crystal molecules showing a smectic A phase in which they are uniaxially aligned; and electrodes disposed on the substrates, wherein transmittance of the liquid crystal layer is adjusted by inclining longitudinal axes of the liquid crystal molecules through applying an electric field to the liquid crystal layer through the electrodes.

According to still yet another embodiment of the present invention, there is provided a liquid crystal spatial light modulation device including a pair of transparent substrates; a liquid crystal layer filled with the liquid crystal molecules according to an embodiment of the present invention and formed between the pair of substrates, the liquid crystal molecules showing a smectic A phase in which they are uniaxially aligned; and electrodes disposed on the substrates, wherein spatial modulation regarding light transmitted through the liquid crystal layer is performed by applying an electric field to the liquid crystal layer through the electrodes.

The liquid crystal molecule according to an embodiment of the present invention shows a smectic A phase in a temperature range in use thereof, shows a large tilt angle in an electroclinic effect, and achieves sufficient optical modulation for use in a liquid crystal display device and a liquid crystal spatial light modulation device.

The liquid crystal display device according to an embodiment of the present invention is bright and excellent in moving-image display quality and has good gradation and high contrast. For example, the display device can be applied to direct-view LCDs and projection display micro liquid crystal devices (liquid crystal on silicon (LCoS) and high-temperature polysilicon TFT-LCDs). In particular, a color display device based on field sequential drive that uses color sequential backlight can be realized.

The liquid crystal spatial light modulation device according to an embodiment of the present invention can achieve three-dimensional display and the like.

DESCRIPTION OF THE PREFERRED EMBODIMENTS

Liquid Crystal Molecule

An embodiment of a liquid crystal molecule according to the present invention will now be described. The liquid crystal molecule according to an embodiment of the present invention has a structure represented by Formula (1):

where $X_1$ in Formula (1) is represented by Formula (2);

$X_2$ in Formula (1) is a group selected from Formula (3); and $X_3$ in Formula (1) is represented by Formula (4).

In Formulas (1) to (4), $R_1$ is a hydrocarbon group or an alkoxy group having a straight chain or a branched chain with 4 to 16 carbon atoms; $R_2$ is an organosiloxane or an organosilane with 1 to 6 silicon atoms that may have a branched chain; $R_3$ and $R_4$ different from each other are each H, F, Cl, Br, CN, $CH_3$, $CF_3$, or $OCH_3$; $Y_1$ and $Y_2$ are each -, —COO—, —$CH_2$—, —$CH_2O$—, —$C_2H_2$—, —$C_2$—, or —$CF_2O$—; $Z_1$ to $Z_4$ are each H, F, Cl, Br, OH, $NO_2$, CN, $CF_3$, $CH_3$, $C_2H_5$, $OCH_3$, or $OC_2H_5$; at least one of $Z_1$ to $Z_4$ is $CH_3$, $C_2H_5$, $OCH_3$, or $OC_2H_5$; $Z_5$ and $Z_6$ are each H, F, Cl, Br, OH, $NO_2$, CN, or $CF_3$; $Z_7$ and $Z_8$ are each H, F, Cl, Br, OH, $NO_2$, CN, or $CF_3$, excluding the case in which both $Z_7$ and $Z_8$ are H; n is an integer from 1 to 6; * represents a chiral center; and -represents a linking group.

The liquid crystal molecule according to an embodiment of the present invention preferably has a structure represented by Formula (5).

In Formula (5), $R_{11}$ is an alkoxy group having a straight chain or a branched chain with 4 to 16 carbon atoms; $R_{13}$ is F, Cl, Br, CN, $CH_3$, $CF_3$, or $OCH_3$; $Z_1$ to $Z_4$ are each H, F, Cl, Br, OH, $NO_2$, CN, $CF_3$, $CH_3$, $C_2H_5$, $OCH_3$, or $OC_2H_5$; at least one of $Z_1$ to $Z_4$ is $CH_3$, $C_2H_5$, $OCH_3$, or $OC_2H_5$; $Z_7$ and $Z_8$ are each H, F, Cl, Br, OH, $NO_2$, CN, or $CF_3$, excluding the case in which both $Z_7$ and $Z_8$ are H; n is an integer from 1 to 6; m is an integer from 1 to 5; and * represents a chiral center.

The liquid crystal molecules according to an embodiment of the present invention form a smectic liquid crystal layer, and preferably show a smectic A phase, for example, at 20 to 50° C., which is a temperature range in which a liquid crystal display device and a liquid crystal spatial light modulation device are used. The smectic liquid crystal layer is formed by arranging liquid crystal molecules in a layered structure (smectic layer) such that their longitudinal axes are oriented in one direction. The smectic A phase herein is such a liquid crystal layer whose normal direction corresponds to the longitudinal directions of liquid crystal molecules.

With the liquid crystal molecules, a tilt angle of 25 degrees or more is achieved due to an electroclinic effect. The liquid crystal layer constituted by the liquid crystal molecules has a transmittance of 60% or more.

Liquid Crystal Display Device

A structure of a liquid crystal display device according to an embodiment of the present invention will now be described. The liquid crystal display device herein is a direct-view display device composed of a liquid crystal material that is directly observed by viewers.

Figure 1:
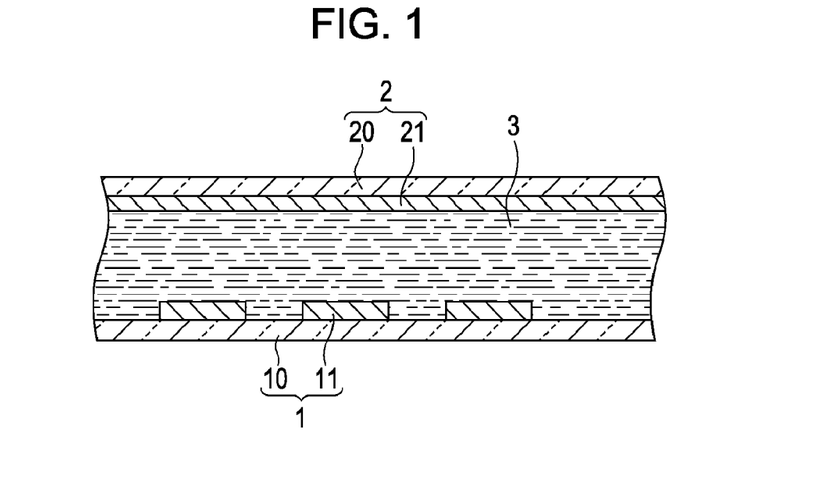
FIG. 1 is a sectional view showing a structure of a liquid crystal display device according to an embodiment of the present invention.

FIG. 1 is a sectional view showing a structure of the liquid crystal display device according to an embodiment of the present invention. The drawing shows principal parts of a transmissive liquid crystal display device, and an active-matrix driving system based on thin film transistor (TFT) driving is adopted.

As shown in FIG. 1, a plurality of switching TFTs are formed on one surface of a first substrate 10 so as to respectively correspond to a plurality of pixels arranged in a matrix. The switching TFTs are connected to pixel electrodes 11 composed of a transparent electrode film such as an indium tin oxide (ITO) film to constitute a TFT array substrate 1. Instead of the switching TFTs, other pixel selecting circuits may be used. In this case, a dielectric film may be disposed on the pixel electrodes 11. A color filter (not shown) is optionally formed on one surface of a second substrate 20, and a counter electrode 21 is entirely formed thereon to constitute a counter substrate 2. Furthermore, a phase difference plate (not shown) and a polarizing plate (not shown) are formed in desired portions of the TFT array substrate 1 and the counter substrate 2.

The TFT array substrate 1 and the counter substrate 2 are bonded to each other through an alignment film (not shown) using a sealing material so as to seal and sandwich a liquid crystal layer 3 composed of a liquid crystal mixture (liquid crystal material) containing the liquid crystal molecules according to an embodiment of the present invention. The liquid crystal molecules according to an embodiment of the present invention show a smectic A phase in which the molecules are uniaxially aligned.

The liquid crystal display device described above includes a backlight unit such as an LED on its back side. In the liquid crystal display device according to an embodiment of the present invention, an inclination (tilt angle) of liquid crystal molecules is changed using a voltage applied between the pixel electrodes 11 and the counter electrode 21 (electroclinic effect) to control transmittance. Consequently, the transmittance of light from the backlight unit can be adjusted. Accordingly, the liquid crystal display device according to an embodiment of the present invention can display an image with gradation.

For example, a 1H inversion driving method (H means a horizontal scanning period) or a 1F inversion driving method (F means a field) can be adopted as a driving method of an image signal. In this AC drive, the color levels (gradation) of liquid crystal can be changed in accordance with the magnitude of driving voltage (magnitude of amplitude). In particular, the contrast of a displayed image can be further improved by increasing the driving voltage.

Since the liquid crystal display device according to an embodiment of the present invention uses the liquid crystal molecules according to an embodiment of the present invention, a bright image that has good moving-image display quality, good gradation, and high contrast can be displayed.

Liquid Crystal Spatial Light Modulation Device

A structure of a liquid crystal spatial light modulation device according to an embodiment of the present invention will now be described.

The liquid crystal spatial light modulation device herein two-dimensionally separates light from a certain light source and changes the intensity, the phase, or the like of the individual fluxes of light. The liquid crystal spatial light modulation device includes, for example, a microdisplay (LCoS) and a light valve used for a projector display or a phase modulation device such as an optical deflection switch. For example, the light valve is obtained by applying the liquid crystal display device shown in FIG. 1. In other words, light emitted from a light source is separated into red light, green light, and blue light, and they are modulated using three light valves constituted by the liquid crystal display device according to an embodiment of the present invention. The modulated fluxes of colored light are then mixed again, and the mixed light is enlarged and projected on a projection surface.

Figure 2:
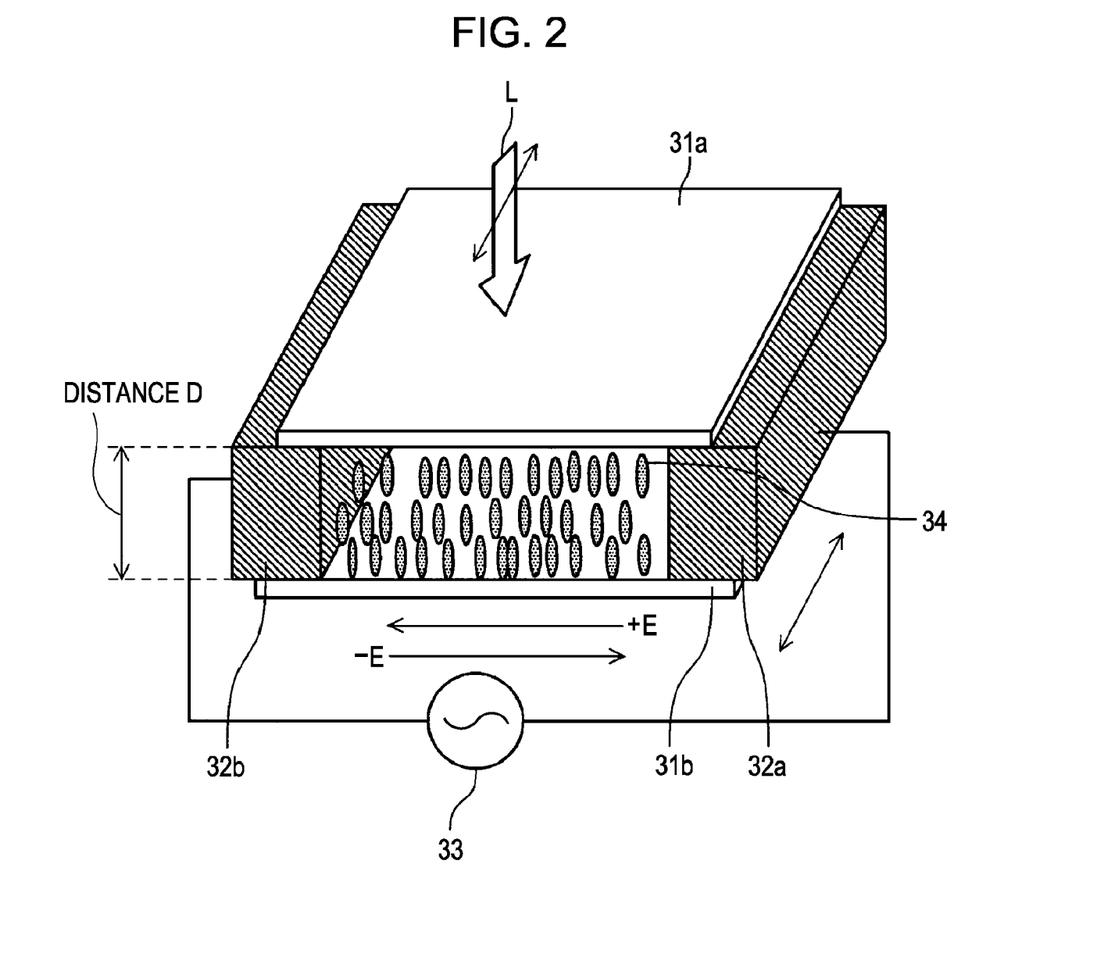
FIG. 2 is a schematic view showing a structure of a liquid crystal spatial light modulation device according to an embodiment of the present invention.

FIG. 2 shows an example of the optical deflection switch as the liquid crystal spatial light modulation device according to an embodiment of the present invention.

As shown in FIG. 2, a pair of transparent substrates 31a and 31b composed of glass or the like are disposed with a certain interval such that their principal surfaces face each other in parallel. A vertical alignment agent that aligns liquid crystal molecules in a vertical direction is applied to the principal surfaces facing each other. Electrodes 32a and 32b are sandwiched between the transparent substrates 31a and 31b at both ends thereof in one direction. An AC electric field is applied between the electrodes 32a and 32b from an external driving device 33 that applies an AC electric field.

Liquid crystal molecules 34 according to an embodiment of the present invention are enclosed between the transparent substrates 31a and 31b. The liquid crystal molecules 34 shows a smectic A phase in an environment in which the liquid crystal spatial light modulation device is used while they are aligned in a direction perpendicular to the principal surfaces of the transparent substrates 31a and 31b because of the vertical alignment agent when an electric field is not applied.

In the liquid crystal spatial light modulation device, incident light L enters from the substrate 31a side in a direction parallel to the normal line of the substrate 31a (in a direction perpendicular to the substrate 31a). The incident light L is deflected in a direction orthogonal to the electric field direction by an electric field applied between the electrodes 32a and 32b before being emitted from the device. For example, when an electric field E=0, the incident light is not shifted. When an electric field E>0, the incident light is shifted in a certain direction (+direction) orthogonal to the electric field direction before being emitted from the device. When an electric field E<0, the incident light is shifted in a direction (−direction) opposite to the direction in the case of E>0 before being emitted from the device. The shift quantity can be adjusted in accordance with the magnitude of the electric field.

EXAMPLES

The present invention will be specifically described with Examples.

Example 1

(1) Synthesis of Liquid Crystal Molecules

The liquid crystal molecules according to an embodiment of the present invention were obtained in the following procedure.

Step 1

A tetrahydrofuran (THF) solution containing 4-bromo-2-fluorophenol, triphenyl phosphine, and (s)-5-hexen-2-ol was inserted into an argon-purged flask. A THF solution containing diethyl azodicarboxylate was dripped into the flask, and the admixture was stirred at a room temperature through the night. After the removal of the solvent, the following intermediate product 1 was obtained using column chromatography.

Intermediate Product 1

Step 2

Dichloro(dicyclopentadienyl)platinum (II) as a catalyst was added to a THF solution containing the intermediate product 1 and 1,1,3,3,3-pentamethyldisiloxane. The admixture was stirred in an argon atmosphere at 60° C. for 24 hours. After the removal of the solvent, the following intermediate product 2 was obtained using column chromatography.

Intermediate Product 2

Step 3

Tetrakis(triphenylphosphine)palladium(0) and a sodium carbonate solution as catalysts were added to an ethylene glycol dimethyl ether solution containing the intermediate product 2 and 4-(4,4,5,5-tetramethyl-1,3,2-dioxaborolan-2-yl)phenol. The admixture was refluxed in a nitrogen atmosphere for 24 hours. After the removal of the solvent, the following intermediate product 3 was obtained using column chromatography.

Intermediate Product 3

Step 4

A dichloromethane solution containing the intermediate product 3, 4-dodecaoxy-3-methylbenzoic acid, and 4-dimethylaminopyridine was added to 1-(3-(dimethylamino)-propyl)-3-ethylcarbodiimide methiodine. The admixture was stirred at a room temperature through the night. The stirred solution was then cleaned with water, separated, and dried with sodium sulfate. After the removal of the solvent, the following end product 4 was obtained using column chromatography.

End Product 4

Figure 3:
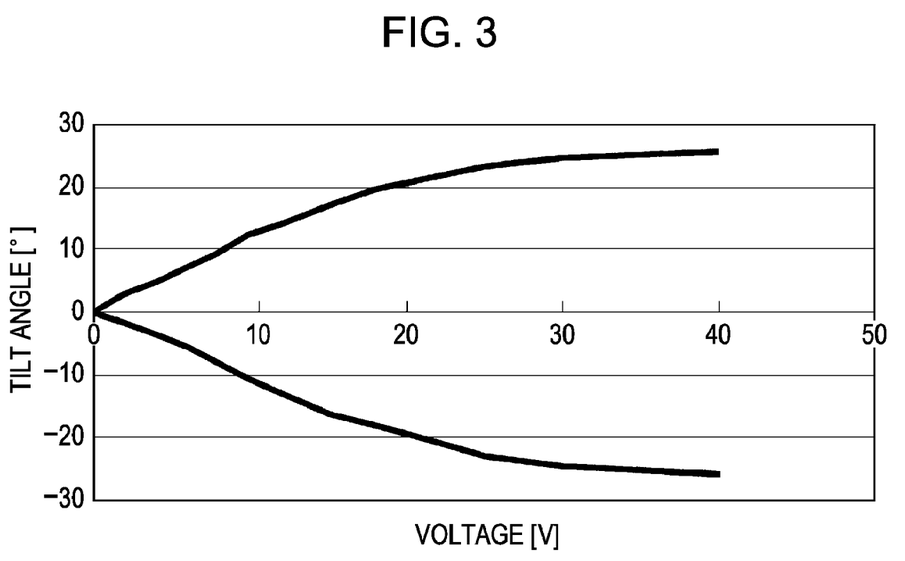
FIG. 3 is a graph showing a relationship between voltage and tilt angle for an evaluation cell in Example 1.

The end product 4 showed a smectic A phase at 40 to 50° C. FIG. 3 shows an applied-voltage dependence of tilt angle at 45° C. To determine phase transition temperature and identify a smectic A phase, differential scanning calorimetry and polarization microscopy with a hot stage were performed.

(2) Making of Evaluation Cell

After a polyimide alignment film was formed on a glass substrate with ITO, a rubbing process was performed using a roller with a buff material. A cell was made using an ultraviolet curable resin in which silica balls having a particle size of 2.4 μm were dispersed. Subsequently, the liquid crystal molecules (end product 4) synthesized by the above method were put into the cell at a temperature at which the liquid crystal molecules show isotropic phase to complete an evaluation cell.

(3) Evaluation of Evaluation Cell

Maximum tilt angle, transmittance, and response time were evaluated for the obtained evaluation cell.

For the maximum tilt angle, the evaluation cell was disposed between polarizing plates orthogonal to each other, and transmitted light amount was measured while a rectangular wave electric field was applied. Half of the angle between the optical axes of the polarizing plate and the evaluation cell, the optical axes providing minimum light amounts in positive and negative polarity electric fields, was defined as a tilt angle.

The transmittance was calculated as follows. The optical axis of a polarizing plate of a polarization microscope was matched with that of the evaluation cell when no electric field was applied. The transmitted light amount when an electric field that provides a maximum tilt angle was applied was then measured using a spectrophotometer with the arrangement of polarizing plates being completely parallel to each other.

A rise time when a voltage that provides a maximum tilt angle was applied stepwise from zero electric field using the same optical arrangement as in the case of the transmittance measurement was defined as the response time.

Comparative Example 1

Figure 4:
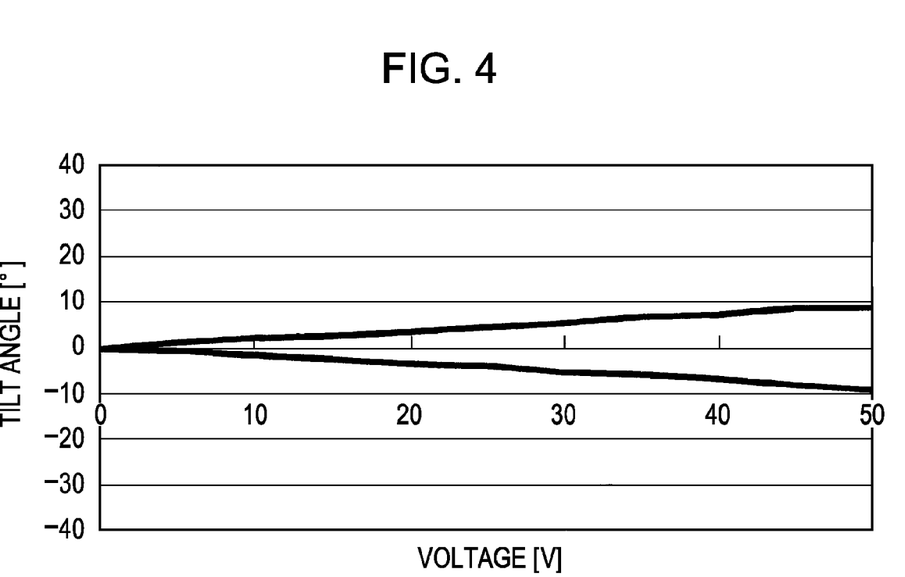
FIG. 4 is a graph showing a relationship between voltage and tilt angle for an evaluation cell in Comparative Example 1.

A synthesis was performed as in Example 1 to obtain an end product 5 except that 4-dodecaoxybenzoic acid was used instead of 4-dodecaoxy-3-methylbenzoic acid in STEP 4 of Example 1. The end product 5 of this Comparative Example showed a smectic A phase at 85 to 95° C. FIG. 4 shows an applied-voltage dependence of tilt angle at 90° C.

End Product 5

Table 1 shows the evaluation results (maximum tilt angles, temperature ranges, and actually measured values of response time) of Example 1 and Comparative Example 1.

TABLE 1

|  | Example 1 | Comparative Example 1 |
| --- | --- | --- |
| Maximum tilt angle | 26° | 9° |
| Temperature range | 40 to 50° C. | 85 to 95° C. |
| Response time | 90 μsec | 200 μsec |

The response time of Comparative Example 1 was of the order of several hundred microseconds. This response time was not sufficiently short for achieving, for example, 240 Hz frame driving (frame time: 4.2 msec). In contrast, the response time of Example 1 was of the order of several tens of microseconds. This response time was sufficiently short for achieving, for example, 240 Hz frame driving.

The maximum tilt angle of Comparative Example 1 was as small as 9° and the transmittance was therefore as low as about 10%. In the case of a liquid crystal display device (LCD), electric power is mostly consumed by a backlight, and a liquid crystal material through which only less than half of light amount can be transmitted poses a serious problem in practical use. In contrast, the tilt angle of Example 1 was 25° or more, and the transmittance was 60% or more. As is evident from comparison with Comparative Example 1, the liquid crystal molecules of Example 1 produced a considerably high effect.

The present application contains subject matter related to that disclosed in Japanese Priority Patent Application JP 2008-253283 filed in the Japan Patent Office on Sep. 30, 2008, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A liquid crystal molecule comprising a structure represented by Formula (1):

wherein $X_1$ in Formula (1) is represented by Formula (2);

$X_2$ in Formula (1) is a group selected from Formula (3);

$X_3$ in Formula (1) is represented by Formula (4); and in Formulas (1) to (4), $R_1$ is a hydrocarbon group or an alkoxy group having a straight chain or a branched chain with 4 to 16 carbon atoms; $R_2$ is an organosiloxane or an organosilane with 1 to 6 silicon atoms that may have a branched chain; $R_3$ and $R_4$ different from each other are each H, F, Cl, Br, CN, $CH_3$, $CF_3$, or $OCH_3$; $Y_1$ and $Y_2$ are each -, —COO—, —$CH_2$—, —$CH_2O$—, —$C_2H_2$—, —$C_2$—, or —$CF_2O$—; $Z_1$ to $Z_4$ are each H, F, Cl, Br, OH, $NO_2$, CN, $CF_3$, $CH_3$, $C_2H_5$, $OCH_3$, or $OC_2H_5$; at least one of $Z_1$ to $Z_4$ is $CH_3$, $C_2H_5$, $OCH_3$, or $OC_2H_5$; $Z_5$ and $Z_6$ are each H, F, Cl, Br, OH, $NO_2$, CN, or $CF_3$; $Z_7$ and $Z_8$ are each H, F, Cl, Br, OH, $NO_2$, CN, or $CF_3$, excluding the case in which both $Z_7$ and $Z_8$ are H; n is an integer from 1 to 6; * represents a chiral center; and - represents a linking group.

2. A liquid crystal molecule comprising a structure represented by Formula (5):

wherein, in Formula (5), $R_{11}$ is an alkoxy group having a straight chain or a branched chain with 4 to 16 carbon atoms; $R_{13}$ is F, Cl, Br, CN, $CH_3$, $CF_3$, or $OCH_3$; $Z_1$ to $Z_4$ are each H, F, Cl, Br, OH, $NO_2$, CN, $CF_3$, $CH_3$, $C_2H_5$, $OCH_3$, or $OC_2H_5$; at least one of $Z_1$ to $Z_4$ is $CH_3$, $C_2H_5$, $OCH_3$, or $OC_2H_5$; $Z_7$ and $Z_8$ are each H, F, Cl, Br, OH, $NO_2$, CN, or $CF_3$, excluding the case in which both $Z_7$ and $Z_8$ are H; n is an integer from 1 to 6; m is an integer from 1 to 5; and * represents a chiral center.

3. A liquid crystal display device comprising:
a pair of transparent substrates;
a liquid crystal layer filled with the liquid crystal molecules of claim 1 or 2 and formed between the pair of substrates, the liquid crystal molecules showing a smectic A phase in which they are uniaxially aligned; and
electrodes disposed on the substrates,
wherein transmittance of the liquid crystal layer is adjusted by inclining longitudinal axes of the liquid crystal molecules through applying an electric field to the liquid crystal layer through the electrodes.

4. A liquid crystal spatial light modulation device comprising:
a pair of transparent substrates;
a liquid crystal layer filled with the liquid crystal molecules of claim 1 or 2 and formed between the pair of substrates, the liquid crystal molecules showing a smectic A phase in which they are uniaxially aligned; and
electrodes disposed on the substrates,
wherein spatial modulation regarding light transmitted through the liquid crystal layer is performed by applying an electric field to the liquid crystal layer through the electrodes.

* * * * *